United States Patent [19]  
Larkin et al.

[11] 4,100,086  
[45] Jul. 11, 1978

[54] DISPERSANT AND LUBE OILS CONTAINING SAME

[75] Inventors: John M. Larkin, Austin, Tex.; Harry Chafetz, Poughkeepsie, N.Y.

[73] Assignee: Texaco Inc., New York, N.Y.

[21] Appl. No.: 735,250

[22] Filed: Oct. 26, 1976

[51] Int. Cl.$^2$ .................. C10M 1/32; C08L 23/36
[52] U.S. Cl. .......................... 252/50; 526/22
[58] Field of Search ............... 252/50; 526/22

[56] References Cited

U.S. PATENT DOCUMENTS

| | | | |
|---|---|---|---|
| 3,300,425 | 1/1967 | Nagelschmidt et al. | 526/22 |
| 3,373,112 | 3/1968 | Anderson et al. | 252/50 |
| 3,565,804 | 2/1971 | Honnen et al. | 252/50 |
| 3,574,576 | 4/1971 | Honnen et al. | 252/50 |
| 3,778,371 | 12/1973 | Malec | 252/34 |
| 3,785,789 | 1/1974 | Honnen et al. | 252/50 |
| 3,822,209 | 7/1974 | Knapp et al. | 252/50 |
| 3,844,958 | 10/1974 | Anderson et al. | 252/50 |

*Primary Examiner*—Delbert E. Gantz
*Assistant Examiner*—Joan Thierstein
*Attorney, Agent, or Firm*—Thomas H. Whaley; Carl G. Ries; Henry W. Archer

[57] ABSTRACT

Disclosed are lube oil dispersants consisting of the reaction products of halogenated polyolefins and aromatic nitrogen heterocycles.

7 Claims, No Drawings

DISPERSANT AND LUBE OILS CONTAINING SAME

BACKGROUND OF THE INVENTION

1. Field of the Invention

This invention relates to a composition of matter synthesized from an excess of aromatic nitrogen heterocycles and halogenated polyolefins and to lubricating oils containing same.

As is well known, during operation of engines using hydrocarbon fuels and lubricants a number of by-products form, including varnish and sludge. Sludge is a mixture of oil, metals and carbon with water which has a mud-like consistency and deposits on the pistons and/or the crankcase. Varnish is an oil-insoluble deposit which forms and adhers on the surfaces of the engine pistons. The formation of sludge and varnish are due, at least in part, to polymerized oxidation products of the oil and fuel.

Many additives have been suggested and tried in fuels and lubricating oils to inhibit the formation of sludge and varnish or to remove these and suspend them in the lubricant until the same is drained out of the equipment.

2. Description of the Prior Art

The preparation of various additives is widely described in the art. Thus the reaction of hydrocarbons with nitrogen-containing compounds is disclosed in U.S. Pat. Nos. 3,293,326, 3,350,381; and 3,481,908. High molecular weight n-hydrocarbyl-substituted quaternary ammonium salts in which the hydrocarbyl groups has a molecular weight of 350-3000 are described in U.S. Pat. No. 3,778,371, as having detergent and dispersant effects on gasoline and lubricating oils.

SUMMARY OF THE INVENTION

The present invention resides in lube oils dispersants prepared by reacting chlorinated polyolefins with nitrogen heterocycle in the present of alkali metal or alkaline earth metal salts.

The compositions of the invention are synthesized as illustrated by the following general equation:

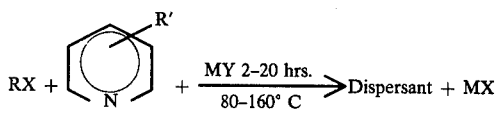

R in this equation can be derived from a polymer of 300-5000 molecular weight such as polypropylene, polybutylene, polyethylene, etc. or copolymers of these materials. X is a halogen, preferably chlorine. MY is a metal salt such as potassium, sodium, magnesium, or calcium oxides, hydroxides, carbonates, bicarbonates, phosphates, nitrates, alkanolates, phenolates, etc. The nitrogen heterocycle can be pyridine, substituted pyridines such as the picolines, nitromethylpyridines, ethyl pyridines, etc., quinolines, isoquinolines, phenazines, purines, pyrimidines, etc., Pyridine and 4-picoline are preferred amines. Sodium carbonate, sodium bicarbonate, sodium hydroxide, and sodium gluconate (or mixtures of these salts) are preferred as MY. A solvent is not necessary, but the use of 0.1-10% of a polar component such as water or a low molecular weight alcohol is preferred.

The aromatic heterocycle is generally used in excess (1.5-30 moles per mole of halogenated polymer) and the metal salt (MY) is generally present in quantities ranging from 0.2-3.0 moles per mole of RX.

The dispersant is isolated by removal of the aromatic heterocycle under reduced pressure and filtration to remove MX and unreacted MY. An extraction step may be employed by partitioning the dispersant between a hydrocarbon such as heptane, gasoline, or diluent oil and methanol. (The methanol portion is discarded or the methanol and the materials it contains can be recycled). After distillation of the hydrocarbon, the dispersant remains.

The infra-red and nmr spectra of many of these products prove that they are not N-alkylammonium salts.

The infrared (IR) and nuclear molecular resonance (NMR) spectra of these products show no bands or only very weak bands characteristics of N-alkyl quaternary heterocyclic salts (e.g., pyridinium salts) and the heterocyclic compound groupings. For instance, the extracted product from the reaction of a chlorinated Indopol H-300 (a polybutylene of about 1230 molecular weight) with pyridine and sodium gluconate shows no pyridine or quaternary pyridinium salt peaks in the infra-red and NMr spectra. The reaction product from chlorinated H-300 made using sodium bicarbonate and 4-picoline; and the nonextracted reaction product of the same chlorinated polybutylene with pyridine and sodium carbonate also show no infra-red or NMR spectra peaks characteristic of quaternary heterocyclic compound salts or heterocyclic compound groupings. Thus, these products are different from those disclosed in U.S. Pat. No. 3,778,371 which employs a procedure leading to N-hydrocarbyl substituted quaternary ammonium salts.

In the oils contemplated herein, the additive compositions normally constitutes between about 0.1 and 10 wt. % of the composition, preferably between about 0.5 and 5 wt. %. Also contemplated are the concentrates thereof wherein the dispersant product content is between about 10 and 50 wt. %. Concentrates are formulated for ease of handling, storage and transportation. The finished lubricating oil compositions are prepared from the concentrates via dilution with additional base oil.

The hydrocarbon base oils employed in major amounts in the finished lubricating oil compositions are derived from a wide variety of hydrocarbon base oil materials such as naphthenic base, paraffinic base and mixed base mineral oils or other hydrocarbon products such as synthetic hydrocarbon oils, e.g. polyalkylenes such as polypropylene, polyisobutylene of a molecular weight of about 250 to 2,500. Advantageously, the base oil employed in the finished lubricating compositions have an SUS viscosity at 100° F. of between about 50 and 2,000, preferably between about 75 and 375.

In the finished lubricating oil compositions of the invention, additional additives such as supplementary detergent-dispersants, oxidation inhibitors, corrosion inhibitors, anti-foamants, etc., may be employed in addition to the disclosed dispersant.

Examples of the supplementary detergent-dispersants contemplated herein are the ethylene oxide derivatives of inorganic phosphorus acid free, steam hydrolyzed polyisobutene (700-5,000 m.w.) $P_2S_5$ reaction product; overbased calcium alkyl aromatic sulfonate having a total base number at least about 300; and sulfurized normal calcium alkylphenolate. These supplementary detergent-dispersants are disclosed in U.S. Pat. Nos. 3,087,956; U.S. Pat. Nos. 3,549,534 and 3,537,966.

Examples of suitable antioxidants contemplated herein are zinc and calcium dialkyl dithiophosphates and diaryl dithiophosphates, the alkylated diphenyl amines, sulfurized alkylated diphenylamines, unsulfurized and sulfurized alkylphenols, phenolates and hindered phenols.

Examples of suitable corrosion inhibitors are zinc dialkyl dithiophosphates, zinc diaryl dithiophosphates, basic calcium, barium and magnesium sulfonates; calcium, barium and magnesium phenolates.

A widely used antifoamant can be included in the finished compositions of the invention, namely the dimethyl silicone polymers normally employed in amounts of between about 1 and 1,000 ppm.

It is also possible to obtain the dispersant of the present invention by omitting the metal salt during the reaction and by employing from 0.15 to 1.5 moles of sodium hydroxide or other base per mole of halogenated polyalkene in the methanol extraction step. The final dispersant has no IR or nmr heterocyclic amine peaks.

Reaction parameters for conducting the invention using the above chlorinated polybutylene are given in the following Table I.

EXAMPLES

The following examples illustrate typical procedures for making some of the products in Table I. The other examples in the Table were carried out in a similar manner. The chlorinated polyisobutylene used in these examples was made by passing chlorine through polyisobutylene of about 1300 mol wt at 125° C until the weight increase accounted for an incorporation of 5.1 to 5.4 wt % chlorine.

EXAMPLE I

A mixture of 260 g of chlorinated polyisobutylene (containing 5.1% Cl), 42.4 g of sodium carbonate and 300 ml of pyridine was refluxed at about 113° C with stirring for 16 hours under a nitrogen atmosphere. The product was diluted with 400 ml of heptane and filtered of 43 g of solids. It was then stripped in a rotary evaporator for about 2 hours at 91° C/1 mm Hg.

EXAMPLES II & III

A mixture of 959 g of sodium gluconate, 24 g of powdered sodium hydroxide, 3000 ml of pyridine, 25 ml of water and 2600 g of chlorinated polyisobutylene (contains 5.1% cl) was refluxed at 110° C for 16 hours with stirring under a nitrogen atmosphere. About 1500 ml of volatile liquid (mostly pyridine) was stripped off at about 20 mm Hg. The product was diluted with 3000 ml of heptane, filtered and finally stripped in a rotary evaporator at 100° C/20 mm Hg to leave 2552 g of product. A 1200 g portion of this product was diluted with 2.5 l of heptane and extracted twice with 2 l portion of methanol. The heptane layer was stripped in a rotary evaporator at 88° C/20 mm Hg.

The following preparations from the table were blended at 5% in the formulation described in the table and were run in the Sequence VC Test with the following results.

| Product | Sludge | Varnish | Piston Skirt Varnish |
| --- | --- | --- | --- |
| Ex. 4 | 9.2 | 7.94 | 7.9 |

This result demonstrates excellent sludge control and varnish control comparable to a standard succinimide type dispersant made from a polybutenylsuccinic anhydride (about 1400 molecular weight) and tetraethylenepentamine when provided in the same formulation at 0.085% nitrogen. A product prepared as was Example 4 also passed the SE specifications in this formulation for the L-38 and IIIC tests and nearly met the SE specification for the sludge engine test (8.2 obtained vs. 8.4 specified), thus demonstrating no marked adverse effect on oxidative stability, rusting or corrosion.

TABLE I

| Example | Metal Salt (MY) | % Cl in Indopol H-300 | Heterocycles (Moles) | Temp. (° C) | Time (Hr.) | Method[1] of Work-up | Mole Ratio MY/RX | Dispersoncy[2] at 4% Conc. Product % Turbidity |
| --- | --- | --- | --- | --- | --- | --- | --- | --- |
| 1 | Na$_2$CO$_3$ | 5.1 | Pyridine (19) | 113 | 16 | Stripped | 2.0 | 14 |
| 2 | Na gluconate | 5.1 | Pyridine (19) | | | Stripped | 2.2 | 10 |
| 3 | & NaOH | | (1% H$_2$O also used) | 110 | 16 | Extracted[a] | | 9 |
| 4 | Na$_2$CO$_3$ | 5.1 | 4-Picoline (6) | 116 | 16 | Extracted | 1.0 | 3.5 |
| 5 | NaHCO$_3$ | 5.1 | 4-Picoline (6) | 118 | 16.5 | Extracted[a] | 1.0 | 24 |
| 6 | Na gluconate | 5.1 | Pyridine (19) (n-butanol (19%) & i-Propanol (25%) also used) | 114 | 16 | Extracted[a] | 2.5 | 3.0 |
| 7 | None | 5.1 | 4-Picoline (5) | 116 | 16 | Extracted (a) with 0.4 mole NaOH in the NeOH | — | 7.0 |
| 8 | | | | | | | | |
| 9 | NaOAc | 5.4 | Pyridine | 114 | 16 | Extracted | 1.5 | 8.0[b] |

[a]Product has no spectral (nmr or ir) pyridine or pyridinium peaks, but does contain nitrogen.
[b]dispersonay determined at 8%.
[1]Stripped means vacuum distillation at about 90° C. followed by filtration of a heptane solution and then vacuum distillation of the heptane; extraction means the heptane solution was washed in MeOH.
[2]dispersonay Test run in a fully formulated reference oil to which the experimental product was added. This test is a measure of dispersance and good dispersants give low % turbidities.

It is to be understood that the foregoing specific examples are presented by way of illustration and explanation only and that the invention is not limited by the details of the examples.

The foregoing is believed to so disclose the present invention that those skilled in the art to which it appertains can, by applying thereto current knowledge, readily modify it for various applications. Therefore, such modifications are intended to fall within the range of equivalence of the appended claims.

What is claimed is:

1. A composition of matter useful as a lubricating oil additive consisting of the reaction product of halogenated polyalkylenes having a molecular weight ranging from about 300 to 5000 or copolymers thereof and an excess of an unsaturated nitrogen containing heterocycle reacted at a temperature of around 80 to 160° C in the presence of an alkali or alkaline earth metal salt; the amount of heterocycle reacted being in excess of 1.5 to 30 moles per mole of said halogenated polyalkylenes with the amount of said metal salt being in an amount ranging from 0.2 to 3.0 moles per mole of said polyalkylenes.

2. The composition of claim 1, wherein said polyalkylene is a chlorinated polyalkylene, said heterocycle is pyridine, picoline, methylethylpyridine, quinoline, isoquinoline, phenazine, purine or pyrimidine and said salt is sodium carbonate, sodium bicarbonate, sodium gluconate or a mixture thereof.

3. A lubricating composition comprising a major portion of a lubricating oil and as an additive an amount of the composition of claim 1 sufficient to provide dispersancy characteristics to said oil.

4. The composition of claim 3, wherein said additive is present in an amount ranging from 0.1 to 10 weight percent.

5. The composition of claim 3, wherein said additive is present in an amount ranging from about 0.5 to 5 weight percent of said composition.

6. The composition of claim 3, wherein said oil has an SUS viscosity at 100° F of between about 50 and 2000.

7. The composition of claim 6, wherein said oil has an SUS viscosity at 100° F of between about 75 and 375.

* * * * *